United States Patent [19]

Piteau et al.

[11] 4,137,253

[45] Jan. 30, 1979

[54] PREPARATION OF CHLOROFORMATES HAVING TERMINAL ACRYLIC OR METHACRYLIC GROUPS

[75] Inventors: Marc D. Piteau, Mennecy; Jean-Pierre G. Senet, Melun, both of France

[73] Assignee: Societe Nationale des Poudres et Explosifs, Paris, France

[21] Appl. No.: 855,183

[22] Filed: Nov. 28, 1977

[30] Foreign Application Priority Data

Dec. 10, 1976 [FR] France .................................. 76 37198

[51] Int. Cl.$^2$ ............................................. C07C 68/02
[52] U.S. Cl. ................................................... 260/463
[58] Field of Search ........................................ 260/463

[56] References Cited

U.S. PATENT DOCUMENTS

| 2,476,637 | 7/1949 | Strain et al. | 260/463 |
| 3,619,260 | 11/1971 | Parker | 260/463 |

FOREIGN PATENT DOCUMENTS

| 495201 | 8/1953 | Canada | 260/463 |
| 629019 | 9/1949 | United Kingdom | 260/463 |

*Primary Examiner*—Elbert L. Roberts
*Assistant Examiner*—Molly C. Eakin
*Attorney, Agent, or Firm*—Bucknam and Archer

[57] ABSTRACT

A process for the preparation of chloroformates having terminal acrylic or methacrylic groups, comprises reacting at least one hydroxyalkyl acrylate or methacrylate with phosgene by introducing a solution of the acrylate or methacrylate into a solution of phosgene, while stirring, at a temperature of $-25°$ C. to $+5°$ C., in the presence of an acid acceptor and a stoichiometric excess of phosgene.

The products thus obtained are monomers suitable for the production of acrylic polymers carrying reactive groups.

7 Claims, No Drawings

PREPARATION OF CHLOROFORMATES HAVING TERMINAL ACRYLIC OR METHACRYLIC GROUPS

The present invention is concerned with a process for the preparation of chloroformates having terminal acrylic or methacrylic groups.

Chloroformates containing terminal acrylic or methacrylic groups are of great industrial value because their polymerisation leads to polymers containing chloroformate groups which are capable of reacting with a wide variety of molecules containing active hydrogen. They are also very useful in forming other acrylic monomers, such as carbonates, carbamates, or acrylic urethane-diols.

A process for the preparation of these valuable chloroformates was proposed as far back as 1949 in British Pat. Specification No. 629,019. This process comprises reacting a hydroxyalkyl acrylate or methacrylate with phosgene at room temperature and in the absence of base. Although the desired chloroformate is obtained by this process, it is unfortunately always in admixture with a significant amount of chlorinated chloroformate.

Since the formation of this chlorinated chloroformate can be attributed to the action of the hydrochloric acid which is liberated during phosgenation, on the double bond of the acrylate or methacrylate group, it has been proposed to use an acid acceptor during the phosgenation.

Thus, French Pat. No. 2,039,075 of 1971 proposes the use of a tertiary amine, pyridine, sodium carbonate, or an alkali metal or alkaline earth metal hydroxide as an acid acceptor in a process in which the phosgenation is carried out by bubbling phosgene into a solution of the hydroxyalkyl acrylate or methacrylate. In this case, although the double bonds of the acrylic or methacrylic groups are well protected from chlorination, only bis-(acryloxyalkyl) carbonates are obtained. Furthermore, if reference is made to U.S. Pat. No. 2,446,145, it will be seen that French Pat. No. 2,039,075 contains contradictions concerning the solvents which can be used and other aspects.

We have now developed a process for the preparation of acrylic or methacrylic chloroformates which gives products which are free of chlorine substitution and substantially free of carbonates.

According to the present invention, there is provided a process for the preparation of chloroformates having terminal acrylic or methacrylic groups, which comprises introducing a solution of at least one hydroxylated acrylate or methacrylate into a solution of phosgene which is in stoichiometric excess, at a temperature of from −20° C. to +5° C., whilst stirring and in the presence of an amount of acid acceptor which is at least equimolecular relative to the hydroxylated acrylate or methacrylate.

Preferred acrylates and methacrylates for use according to the invention are those of the formula:

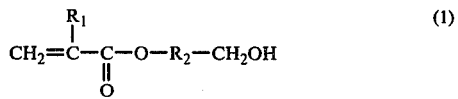

(1)

in which $R_1$ is a hydrogen atom (acrylates) or a methyl group (methacrylates), and $R_2$ is a linear or branched alkylene chain which is optionally substituted by one or more halogens, nitrile or nitro groups, or acrylate or methacrylate groups, and which contains a total of from 1 to 10 carbon atoms and which optionally contains one or more ether bridges.

Any suitable acid acceptor which does not react with phosgene may be used in the process according to the invention; it is preferred to use organic bases, particularly tertiary alkylamines, such as triethylamine, and heterocyclic amines of aromatic character, such as pyridine.

A significant characteristic of the present invention is the order in which the reactants are brought together. We have found that it is of critical importance to introduce the acrylate or methacrylate into the phosgene solution.

For this purpose, the phosgene solution is prepared in an inert solvent, which is preferably one which can be readily removed, such as methylene chloride or ethyl acetate, so as to obtain a solution which is not too dilute, for example, such that the weight ratio of solvent to phosgene is about 1 to 5:1.

The acrylate or methacrylate is dissolved in the same solvent or in a solvent which is miscible with the solvent in which the phosgene is dissolved.

The acid acceptor is preferably introduced into the acrylate or methacrylate solution and is used in an amount which is at least equal to the theoretical amount necessary for the neutralisation of all the hydrochloric acid which can be liberated.

It is preferred to introduce the acrylate or methacrylate solution slowly into the phosgene solution, whilst stirring and keeping the temperature below −10° C.

Another significant characteristic of the process according to the invention is that the phosgene is present in excess relative to the hydroxyl groups of the acrylate or methacrylate. The molar excess of phosgene is preferably at least 10% relative to the hydroxyl groups carried by the acrylate or methacrylate; however, an excess of more than 100% serves no useful purpose, although it is not disadvantageous for the reaction. An excess of 15 to 30% of phosgene is advantageously used.

Once the introduction of the acrylate or methacrylate solution has been completed, the reaction is completed by continuing to stir the reaction mixture at from −20° to +5° C., for a period of time which becomes longer as the amount of reactants becomes larger. The excess phosgene is then removed, for example, by degassing the reaction mixture with an inert gas, which is preferably nitrogen.

The organic phase obtained is then washed, preferably first with acidified water followed by neutral water, separated from the aqueous phase, dried over an anhydrous inorganic salt, and then subjected to purification. The latter preferably consists in distilling the solvent in vacuo.

The desired acrylate or methacrylate chloroformate is normally obtained in a yield of at least 85%. The purity of the chloroformate obtained is always greater than 85%, and generally greater than 90%. The main impurity consists of the corresponding bis-(acryloxyalkyl) carbonate, which readily copolymerises with the chloroformate, but does not impart subsequently reactive groups to the polymer.

It should be noted that the process according to the invention can also be applied to a mixture of hydroxyalkyl acrylates and/or hydroxyalkyl methacrylates. A mixture of the corresponding chloroformates, which are capable of being copolymerised, is then obtained without modifying the process.

The invention provides a considerable technical advance over the art because it enables chloroformates having terminal acrylic or methacrylic groups, which have a high degree of purity and are not mixed with chlorinated chloroformates which cannot be polymerised by a radical process and are difficult to separate, nor mixed with a substantial proportion of carbonate which can be polymerised, but which does not impart subsequent activity to the polymer, to be obtained. In this respect, it must be pointed out that the difficulty which is overcome by the invention becomes greater as the acrylic or methacrylic groups become closer to the reactive hydroxyl group.

In order that the invention may be more fully understood, the following examples are given by way of illustration only:

EXAMPLE 1

Preparation of hydroxyethyl methacrylate chloroformate

A solution of 50 cm$^3$ of phosgene (0.7 mol) in 100 cm$^3$ of methylene chloride was prepared in a one liter four-necked round-bottomed flask provided with a dry ice cooler, a thermometer, a mechanical stirrer and a dropping funnel. A mixture comprising 65 g (0.5 mol) of 2-hydroxyethyl methacrylate and 51 g (0.5 mol) of triethylamine in 100 cm$^3$ of methylene chloride was added to this solution, cooled to $-15°$ C. After one hour of stirring at 0° C., the excess phosgene was removed by bubbling nitrogen. The reaction mixture was then washed in the cold with acidified water, and then with pure water. After drying the organic phase over sodium sulphate and evaporating the solvent under reduced pressure at 30° C., ethyl methacrylate chloroformate was obtained in a yield of 96%.

Ethyl methacrylate chloroformate was identified by its infra-red and NMR spectra:

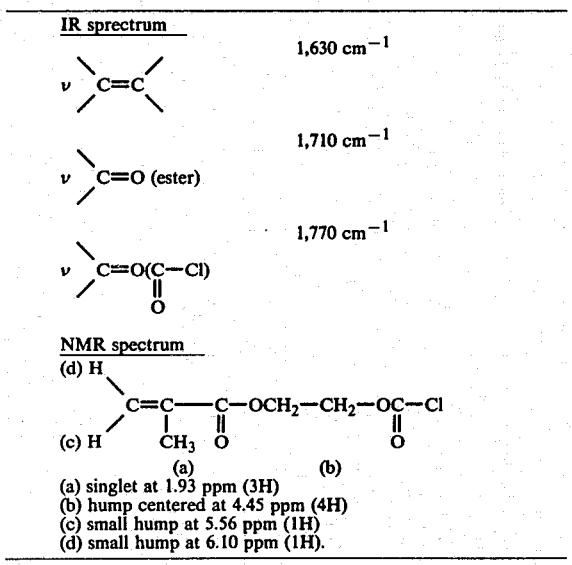

Gravimetric analysis showed that the chlorine content was 16.7, instead of the theoretical value of 18.4, which indicated a purity of 91%. The excess of phosgene relative to the stoichiometric amount was 40%.

EXAMPLE 2

Preparation of hydroxyethyl methacrylate chloroformate 750 g (6 mols + 25%) of phosgene and 2 liters of dry, ethanol-free methylene chloride were placed in a 10 liter reactor, cooled to $-30°$ C. A solution of 6 mols (780 g) of hydroxyethyl methacrylate and 6 mols (480 g) of pyridine in 1 liter of methylene chloride was added to this mixture over a period of 1 hour 30 minutes, the temperature being kept at between $-10°$ and $-15°$ C. After two hours of stirring at $-10°$ C., the excess phosgene was removed by degassing with nitrogen. After removing the pyridine hydrochloride by filtration, the solution was rapidly washed with 2 liters of ice-cold water. The organic phase was decanted, dried over magnesium sulphate and concentrated under reduced pressure; 1,040 g of ethyl methacrylate chloroformate were thus obtained in a yield of 90%.

The chlorine content of the product obtained was 16.8%, instead of the theoretical value of 18.4%, which indicated a degree of purity of 92%.

EXAMPLE 3

Preparation of a mixture of acrylic chloroformates

In this example, a mixture of 85% of hydroxyethyl acrylate and 15% of 2-hydroxy-1-ethoxyethyl acrylate was used as the starting material.

1.15 mol of phosgene dissolved in 150 ml of dry methylene chloride were placed in a 1 liter reactor. A mixture consisting of 116 g of the said acrylic alcohol mixture (1 mol of hydroxyl), 80 g (1 mol) of pyridine and 150 ml of methylene chloride was then added at $-15°$ C. The mixture was allowed to return to room temperature and the excess phosgene (15%) was removed by degassing with nitrogen.

After filtration, the organic solution was washed with acidified water and neutral water, and then dried and concentrated under reduced pressure. 156.4 g of the desired product were obtained, that is to say a yield of 88%.

The NMR spectrum showed a mixture of chloroformates:

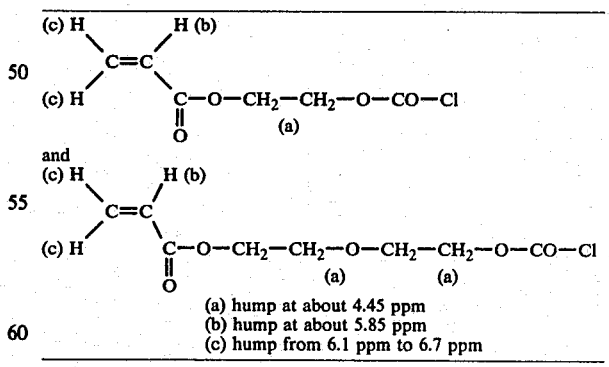

The chlorine content found was 17.7%, compared with the theoretical value of 19.1. The mixture therefore contained 93% of chloroformates.

What is claimed is:

1. A process for the preparation of a chloroformate of formula

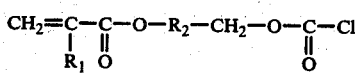

wherein $R_1$ is hydrogen or methyl and $R_2$ is an alkylene of 1 to 10 carbon atoms which consists of introducing a solution of one acrylate or methacrylate of formula

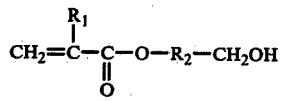

wherein $R_1$ and $R_2$ are as defined hereinabove and an acid acceptor selected from the group consisting of tertiary alkylamines and heterocyclic amines of aromatic character, in an inert solvent into a solution of phosgene in the same inert solvent or in a solvent which is miscible with said solvent, said phosgene being present in an at least 10% excess with respect to the stoichiometric amount, at a temperature of from $-20°$ C. to $+5°$ C., while stirring, and isolating said chloroformate from the reaction mixture.

2. A process according to claim 1 wherein at least two said acrylate or methacrylate in solution in said inert solvent are introduced into said solution of phosgene and a mixture of at least two chloroformates is obtained.

3. A process as set forth in claim 1 wherein the ratio by weight of the inert solvent to phosgene is between 1 and 5:1.

4. A process as set forth in claim 1 wherein the phosgene is present in a molar excess between 15 and 30% with respect to the stoichiometric amount.

5. A process as set forth in claim 1, wherein $R_2$ is an alkylene substituted by at least one substituent selected from the group consisting of halogen atoms, nitrile, nitro, acrylate and methacrylate groups.

6. A process as set forth in claim 1, wherein $R_2$ is an alkylene which contains at least one ether linkage.

7. A process as set forth in claim 1, wherein said acid acceptor is selected from the group consisting of triethylamine and pyridine.

* * * * *